(12) United States Patent
Shiue

(10) Patent No.: US 7,992,227 B2
(45) Date of Patent: Aug. 9, 2011

(54) FRAME STRUCTURE OF LENSES

(75) Inventor: Chih-Cheng Shiue, Taipei (TW)

(73) Assignee: QBAS Co., Ltd., Taipei (TW)

( * ) Notice: Subject to any disclaimer, the term of this patent is extended or adjusted under 35 U.S.C. 154(b) by 643 days.

(21) Appl. No.: 11/955,636

(22) Filed: Dec. 13, 2007

(65) Prior Publication Data

US 2009/0038061 A1    Feb. 12, 2009

(30) Foreign Application Priority Data

Aug. 9, 2007 (TW) .............................. 96213120 U

(51) Int. Cl.
*A61F 9/02* (2006.01)
(52) U.S. Cl. ............................................ 2/445; 351/43
(58) Field of Classification Search ............... 2/440, 441, 2/450; 351/51, 90, 43
See application file for complete search history.

(56) References Cited

U.S. PATENT DOCUMENTS

| 6,253,387 | B1* | 7/2001 | Yu ..................................... 2/428 |
| 6,969,172 | B2* | 11/2005 | Actis-Datta ..................... 351/86 |
| 2005/0120468 | A1* | 6/2005 | Kawashima et al. ............. 2/444 |
| 2005/0273913 | A1* | 12/2005 | Chiang ............................. 2/428 |
| 2006/0117469 | A1* | 6/2006 | Garofalo et al. .................. 2/428 |
| 2007/0024806 | A1* | 2/2007 | Blanshay et al. ............... 351/62 |
| 2008/0086797 | A1* | 4/2008 | Shiue ............................... 2/440 |

* cited by examiner

*Primary Examiner* — Katherine Moran
(74) *Attorney, Agent, or Firm* — Dariush G. Adli; Adli Law Group P.C.

(57) ABSTRACT

A frame structure for use in goggles is disclosed. The frame structure comprises a main body, which comprises a hard portion and a soft portion. The hard portion is a rigid body, while the soft portion is an elastomer. The soft and the hard portions are molded integrally, wherein the integrally molded portions define at least one receiving space and is adapted to receive at least one lens.

14 Claims, 9 Drawing Sheets

FRAME STRUCTURE OF LENSES

RELATED APPLICATION(S)

This application claims the benefit of priority based on Taiwan Patent Application No. 096213120 filed on 9 Aug. 2007, the disclosure of which is incorporated herein by reference in its entirety.

BACKGROUND OF THE INVENTION

1. Field of the Invention

The subject invention relates to a frame structure, and more particularly, relates to a frame structure for use in a swimming goggles.

2. Descriptions of the Related Art

Goggles currently used in diving, skiing or similar sports provide protection and appropriate isolation from the exterior environment for users. Goggles used in diving masks must provide a superior waterproof function under high water pressure in deep water. Therefore, various parts of the diving goggles must be connected closely with each other to adequately perform the isolation and protection functions thereof; otherwise, if the parts fail to form a tight assembly, crevices would be formed at junctions between the individual parts. As a result, the user is exposed to water leakage.

For example, a diving goggle of the prior art is typically comprised of several key parts. More specifically, referring to FIG. 1A and FIG. 1B, a conventional diving goggle is comprised of a diving mask 10 and a frame structure 20. The frame structure 20 mainly comprises an upper frame portion 22, a lower frame portion 24 and several joints 26. The upper and lower frame portions 22, 24 independent from each other are combined into a complete frame by several joints 26 bridging therebetween respectively, and define two receiving spaces for receiving two pieces of lens.

The conventional frame structure 20 has a complete frame separated into the independent upper and lower frame portions 22, 24 mainly for the sake of convenience during the assembly of lenses. Specifically, because the conventional upper and lower frame portions 22, 24 are generally made of hard materials, the frame formed when assembled together is an undeformable rigid structure, which is undesirable for assembling lenses into the receiving spaces of the frame. To prevent this problem, in the frame structure 20 of conventional diving goggles, the frame has independent upper and lower frame portions 22, 24, with two gaps formed at the junction points of opposite ends of the two frame portions to enhance the flexibility of the frame. As a result, the lenses may be assembled readily into the receiving spaces of the frame, and the joints 26 are finally bridged therebetween to obtain a complete frame.

Although such a combined frame structure 20 facilitates the assembly of lenses, it does not have a tight assembly. For example, a crevice 29 may be formed around the junction point in the central nose area 28 (the area shown by the dashed line in FIG. 1) of the upper and the lower frame portions 22, 24. Due to the poor tightness, water may leak through under deep water where there is high water pressure. Accordingly, to enhance the tightness of the conventional combined frame structure 20, a fixing mount 30 and a locking device 32 (e.g., a screw) are added to the central nose area 28 of the upper and the lower frame portions 22, 24. However, such a combined frame structure 20 with a fixing mount 30 not only entails a complex manufacturing process, but also has an increased number of parts, which results in higher costs and higher possibility of losing parts. Therefore, a new frame structure with easy assembly, simple structure, and superior water proof structure, is needed.

SUMMARY OF THE INVENTION

One objective of the subject invention is to provide a frame structure for use in a goggle, which not only provides an the appropriate protection for the user, but also features easy assembly and assembly easiness and simple structure.

To this end, the frame structure of this invention comprises a main body, which comprises a hard portion and a soft portion. The hard portion is a rigid body, while the soft portion is an elastomer. The soft portion is either molded integrally or connected to the hard portion, wherein the hard portion and the soft portion define at least one receiving space adapted to receive at least one lens.

The detailed technology and preferred embodiments implemented for the subject invention are described in the following paragraphs accompanying the appended figures for people skilled in this field to well appreciate the features of the claimed invention.

DESCRIPTION OF THE PREFERRED EMBODIMENT

The following description is directed to the frame structure for use in a goggle, and particularly to a frame structure for use in a swimming or diving goggle. However, it can be appreciated that the use of the frame structure disclosed in this invention is not just limited to diving sports, and appropriate alterations or modifications may be made thereto by those skilled in the art in light of the spirit and principle of this inventions. Therefore, such alterations and modifications shall be considered to still fall within the scope of the claims set forth in this invention.

Figure 2A:
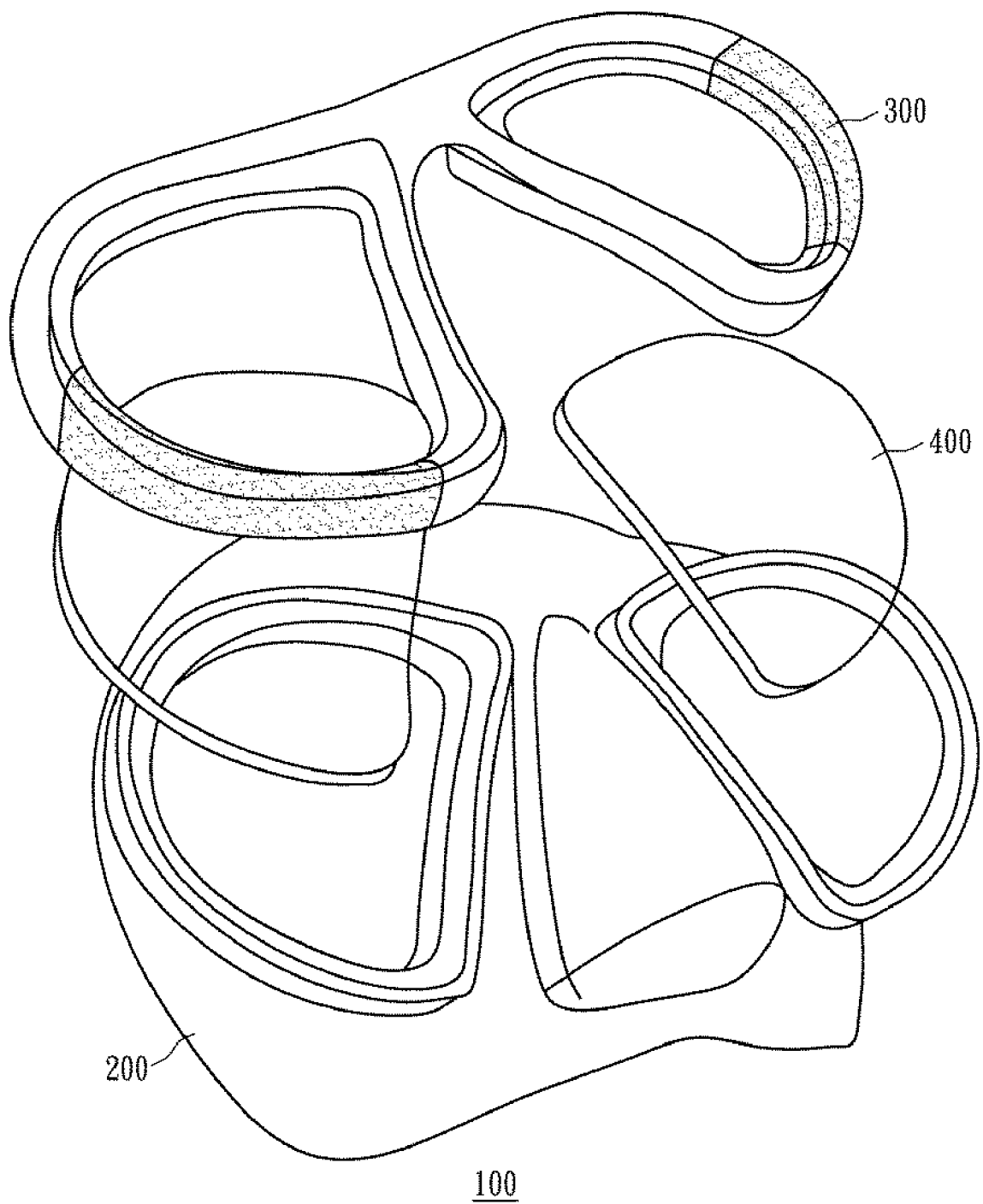
FIG. 2A and FIG. 2B are schematic views of a diving goggle in an embodiment of this invention.
Figure 2B:
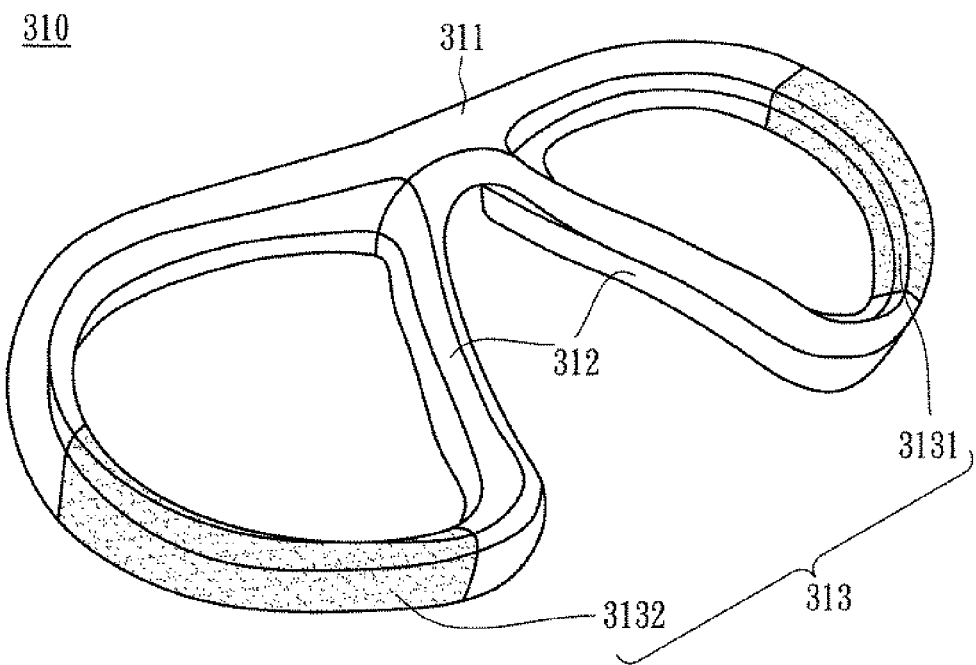

In reference to FIGS. 2A and 2B, an embodiment of the diving goggle used in this invention is depicted. The diving goggle 100 of this invention comprises a diving mask 200, a frame structure 300 and two lenses 400. Specifically, the frame structure 300 comprises a main body 310, which further comprises an upper bridge portion 311, a nose portion 312 and a frame portion 313. The nose portion 312 extends downwards from a central area of the upper bridge portion 311, while the frame portion 313 has a first frame 3131 and a second frame 3132. The first frame 3131 is formed between the upper bridge portion 311 and the nose bridge 312 at one side, while the second frame 3132 is formed between the upper bridge portion 311 and the nose portion 312 at the opposite side.

Figure 3:
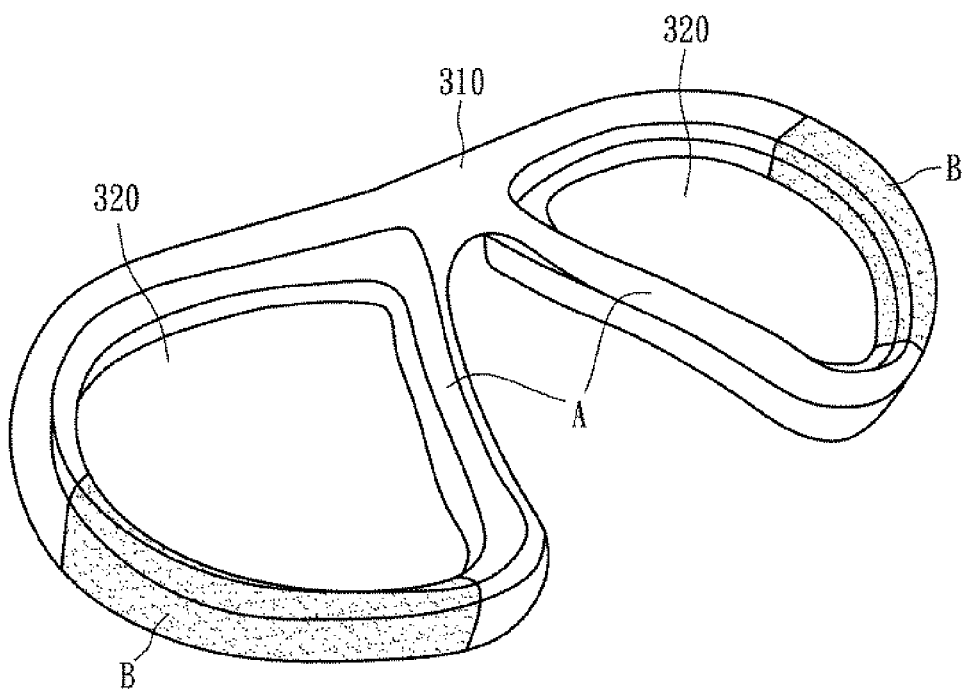
FIG. 3 is a schematic view of a main body in an embodiment of this invention.

As shown in FIG. 3, the main body 310 of the frame structure 300 in an embodiment of this invention is depicted. In terms of the materials thereof, one feature of the main body 310 of this invention is that it comprises a hard portion A and a soft portion B, wherein the hard portion A is a rigid body and the soft portion B is an elastomer. In the preferred implementation, the aforesaid hard portion A is made of materials selected from a group consisting of polycarbonate (PC), polyethylene (PE), polyoxomethylene (POM), resin, acrylic, polyurethane (PU), polyvinyl chloride (PVC), acrylonitrile butadiene styrene (ABS), polypropylene (PP), nylon, metals, and or combinations thereof. One the other hand, the aforesaid soft portion B is made of materials selected from a group consisting of thermoplastic rubber (TPR), thermoplastic polyurethane (TPU), thermoplastic elastomer (TPE), polyurethane (PU), polyvinylchloride (PVC), silicone, nature rubber and or combinations thereof. Any soft materials proper for being combined with the hard portion A can be applied in the soft portion B.

It should be noted that different from the conventional combined frame structure with two independent upper and lower frame portions, the hard portion A and the soft portion B of the frame structure 300 of this invention are molded integrally to ensure that no crevice exists therebetween. The hard portion A and the soft portion B together define two receiving spaces 320 adapted to receive two lens 400 respectively in a sealing or seamless manner. Additionally, the integrally molded two portions are formed in sequence in a mold by overmolding or multi-material injection molding, with the hard portion A and the soft portion B joined together tightly.

It can be known from the above description that because the main body 310 of this invention is an integrally molded structure, the risk of water leakage under deep waters is prevented. On the other hand, with the combination of the rigid hard portion A and a deformable soft portion B, the main body 310 not only has a strength provided by the rigid body, but also has a plasticity provided by the elastomer. Therefore, when assembling the lenses 400 into the frame structure 300 of this invention, the lenses 400 can be assembled readily into the receiving spaces 320 defined by the main body 310, without any gaps in the main body.

Alternatively, in other implementations, the soft portion B of the main body 310 may also be connected to the hard portion A in other joining manners such as in a mechanical locking manner. For example, the main body 310 may further comprise a connecting assembly (not shown) used to connect the soft portion to the hard portion. Here, the connecting assembly may comprise a raised portion and a recess disposed in either of the hard portion A and the soft portion B respectively. With the raised portion engaged into the recess, the soft portion B may be sealed into the hard portion A. At least one receiving space defined by the two portions may be adapted to receive at least one lens in a sealing manner, so that the goggle utilizing this invention is suitable for use under deep waters. Alternatively, the soft portion B of this invention may also be adhered to the hard portion A with an adhesive or the soft portion B may also be connected to the hard portion A by using the adhesive together with the connecting assembly as mentioned above.

The aforesaid frame structure of this invention is only one of several implementations of this invention, and alterations or modifications may be made thereto by those skilled in the art upon reading the above description. Further, the following embodiments are only intended to illustrate variations of this invention in practical use, rather than to limit the scope of this invention.

Figure 4A:
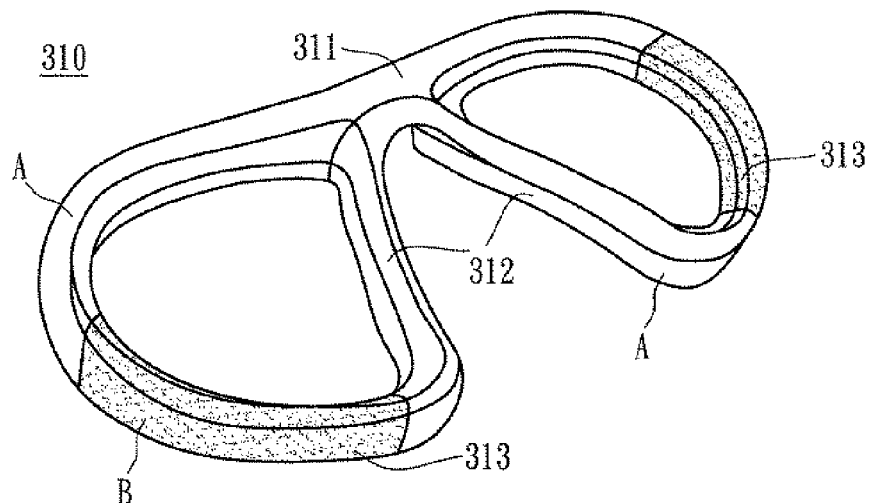
FIGS. 4A to 4F are schematic views showing variations of the materials of a main body in several embodiments of this invention.
Figure 4B:
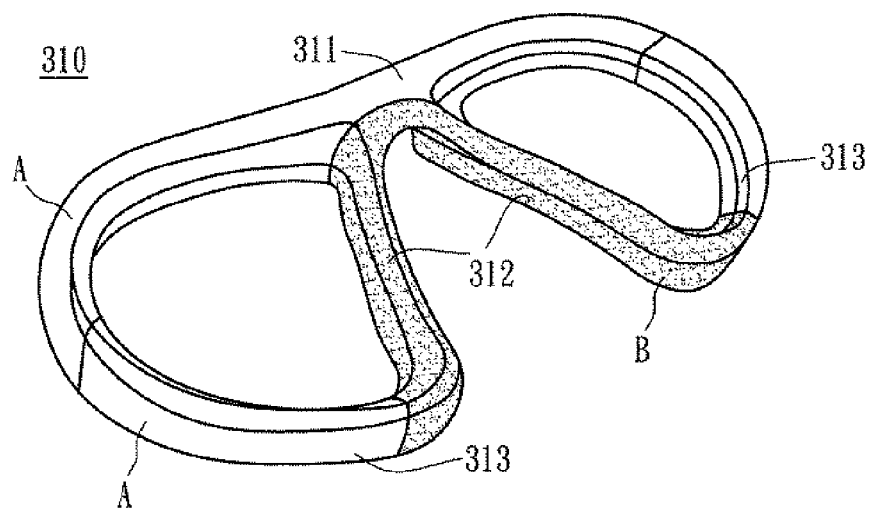
Figure 4C:
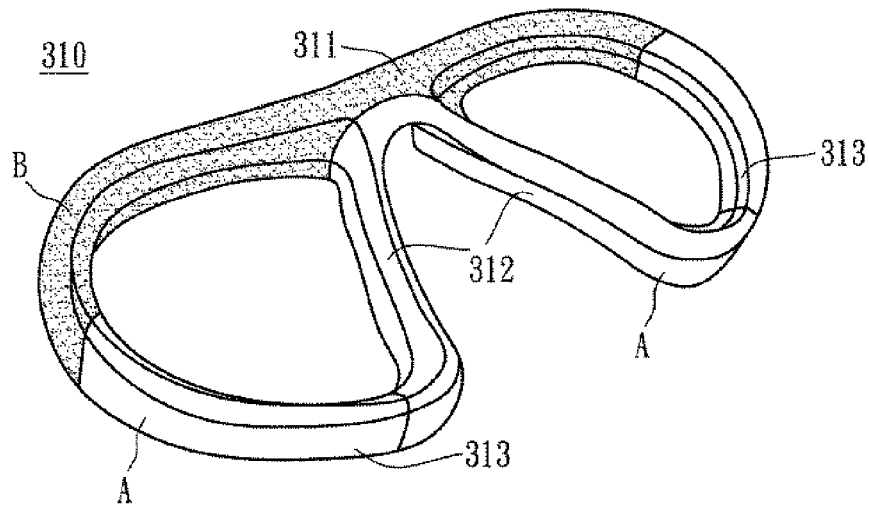
Figure 4D:
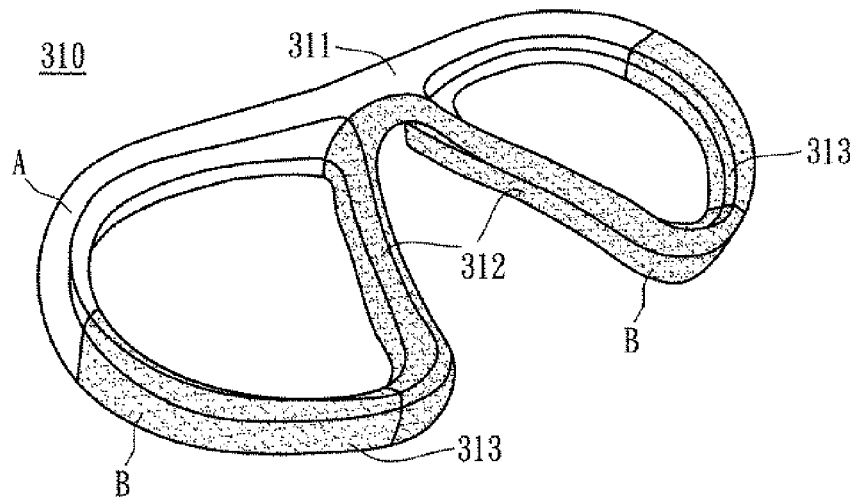
Figure 4E:
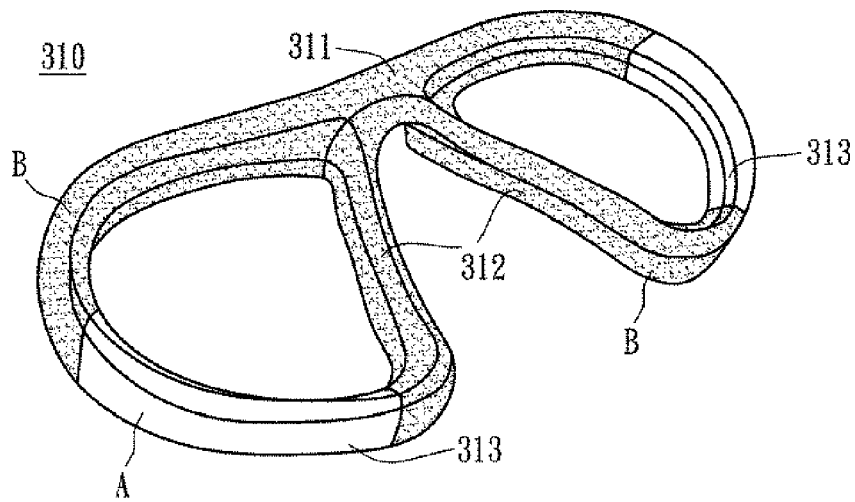
Figure 4F:
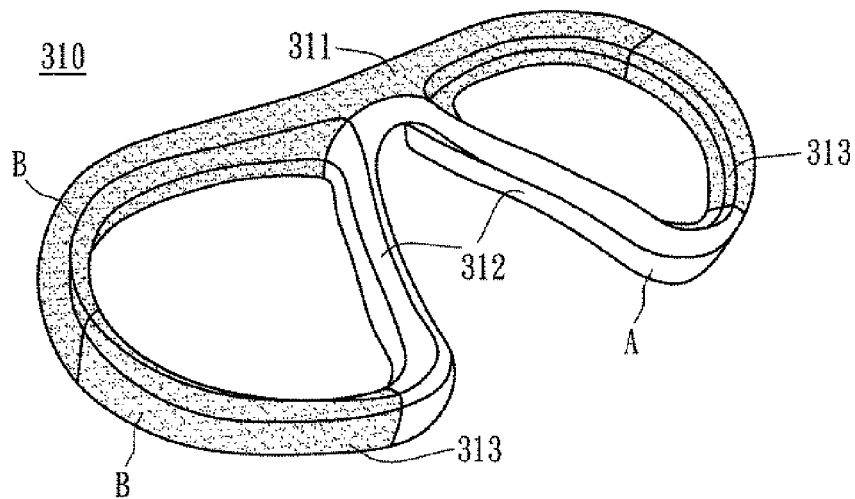

FIGS. 4A to 4C illustrate several variations in terms of the materials of the main body 310 are depicted. Specifically, depending on the actual requirements on the overall rigidity and flexibility of the main body 310, the soft portion B may be formed in the upper bridge portion 311, the nose portion 312 and the frame portion 313, while the hard portion A may be formed in the remaining portions. Alternatively, as shown in FIGS. 4D to 4F, the soft portion B may be formed in two of the upper bridge portion 311, the nose portion 312 and the frame portion 313, with the hard portion A formed in the remaining portions. These and other similar variations all fall within several possible implementations of this invention. Especially, in conjunction with the overall profile of the diving goggle, an appropriate adjustment may be made between the soft portion B and the hard portion A to endue the main body 310 with aesthetic and diversified appearances.

Figure 5A:
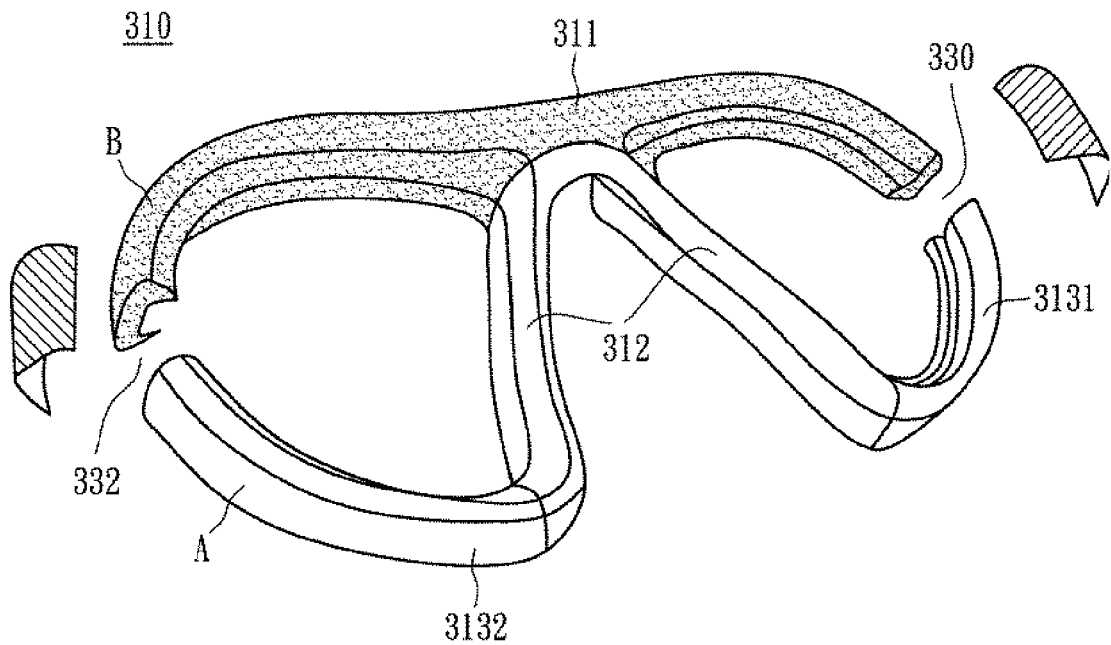
FIGS. 5A to 5D are schematic views of a main body with gaps disposed therein in several embodiments of this invention.
Figure 5B:
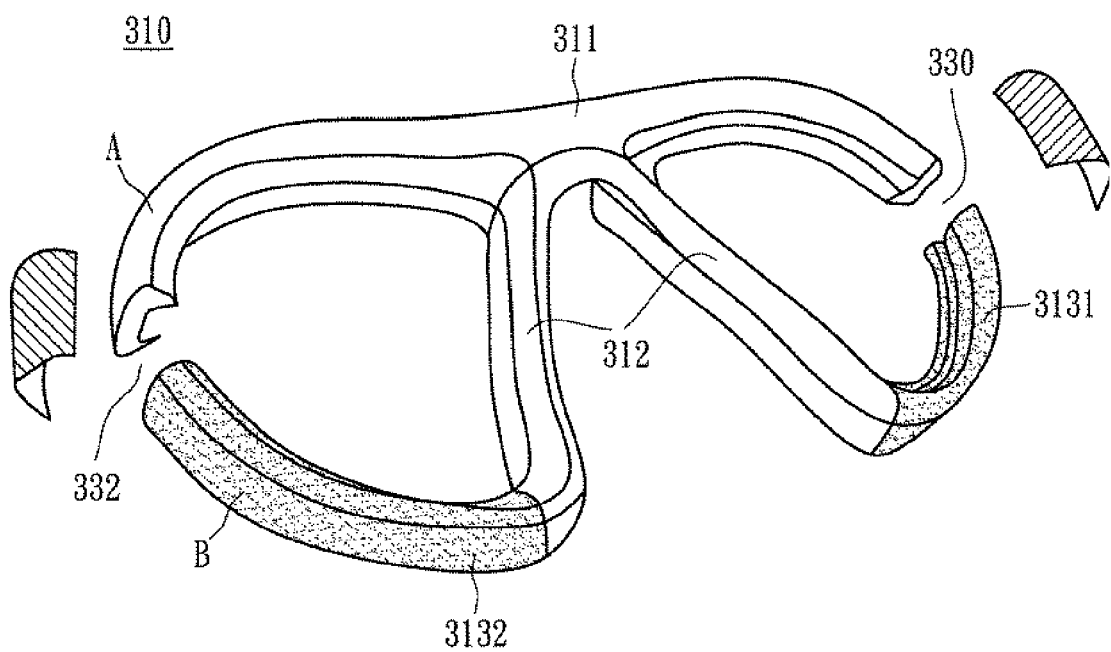

Additionally, gaps may be disposed at appropriate locations of the main body 310 of this invention to further increase the flexibility thereof. For example, when the soft portion B is formed in one of the upper bridge portion 311, the nose portion 312 and the frame portion 313, the soft portion B comprises the upper bridge portion 311 while the hard portion A comprises the nose portion 312 and the frame portion 313. The first gap 330 would then be disposed between the upper bridge portion 311 and the first frame 3131, while the second gap 332 may be disposed between the upper bridge portion 311 and the second frame 3132, as shown in FIG. 5A. On the other hand, when the soft portion B comprises the frame portion 313 and the hard portion A comprises the upper bridge portion 311 and the nose portion 312, the first gap 330 may be disposed between the upper bridge portion 311 and the first frame 3131. Likewise, the second gap 332 may be disposed between the upper bridge portion 311 and the second frame 3132, as shown in FIG. 5B.

Figure 5C:
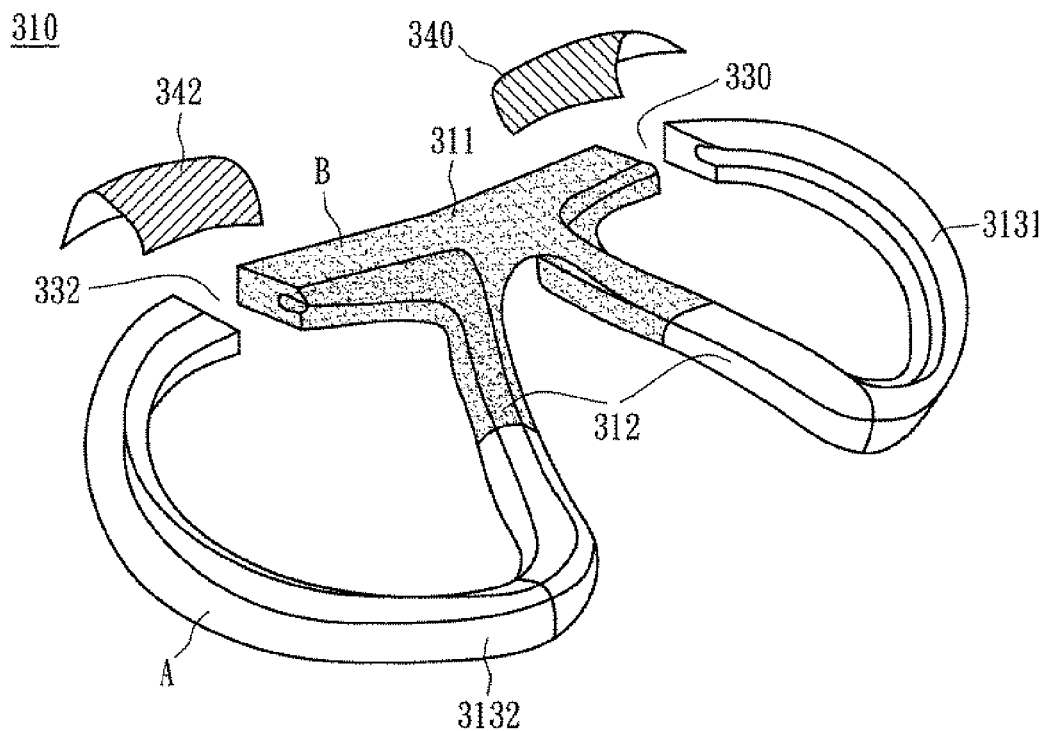
Figure 5D:
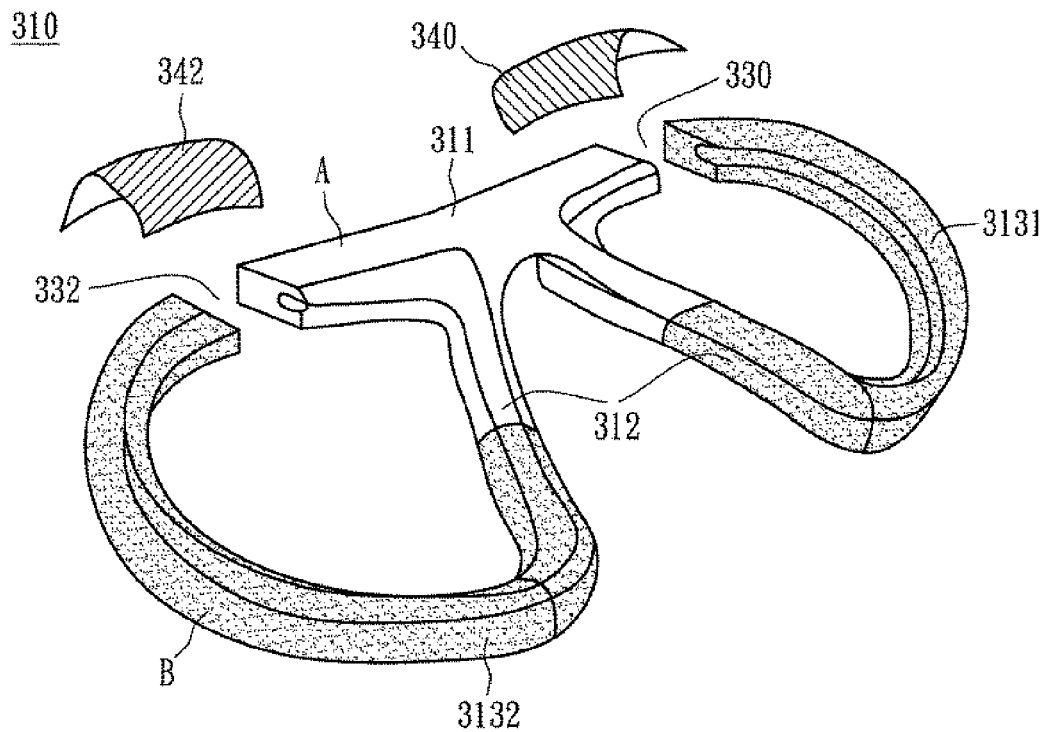

When the main body 310 has the soft portion B formed in two of the upper bridge portion 311, the nose portion 312 and the frame portion 313, the soft portion B comprises the upper bridge portion 311 and a part of the nose portion 312, while the hard portion A comprises the frame portion 313 and the other part of the nose portion 312. The first gap 330 may be disposed between the upper bridge portion 311 and the first frame 3131, and a second gap 332 may be disposed between the upper bridge portion 311 and the second frame 3132, as shown in FIG. 5C. On the other hand, when the soft portion B comprises the frame portion 313 and a part of the nose portion 312, and the hard portion A comprises the upper bridge portion 311 and the other part of the nose portion 312, the first gap 330 may be disposed between the upper bridge portion 311 and the first frame 3131, while the second gap 332 may be disposed between the upper bridge portion 311 and the second frame 3132, as shown in FIG. 5D.

Figure 6A:
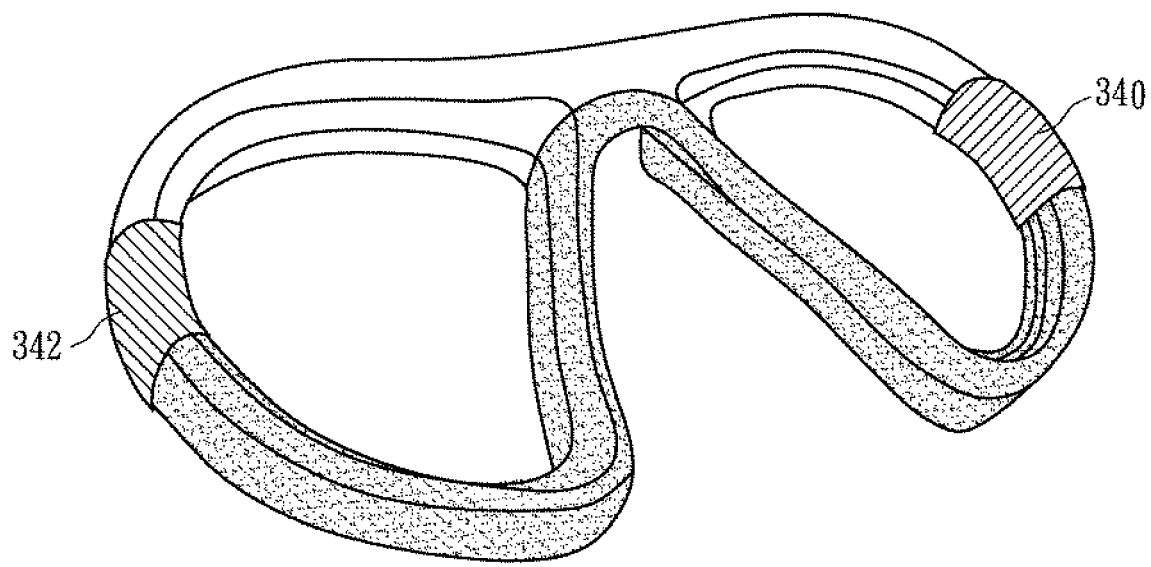
FIGS. 6A and 6B are schematic views of a main body with decorative joints in several embodiments of this invention.
Figure 6B:
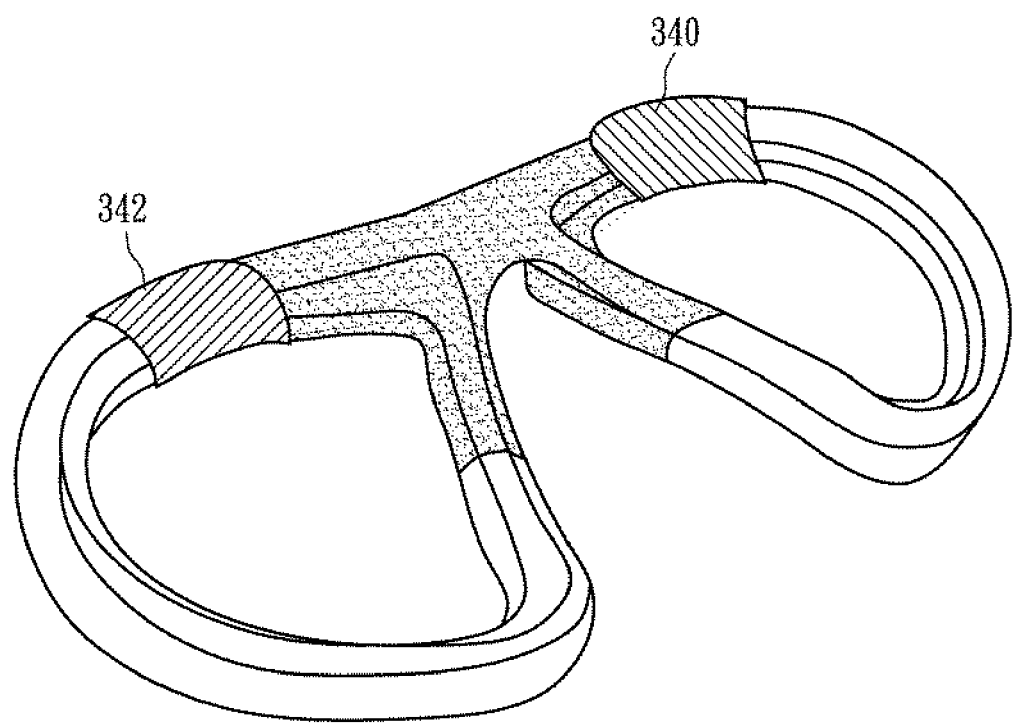

Further, as shown in FIGS. 5A to FIG. 5D, the first gap 330 and second gap 332 are disposed in the main body 310, while the frame structure 300 of this invention further comprises a first joint 340 and a second joint 342 to close the first gap 330 and the second gap 332 respectively after two lens 400 are received in the main body. In the preferred embodiment, both the first joint 340 and the second joint 342 have a respective decorative surface to be used in conjunction with the design of the diving goggle, as shown in FIGS. 6A to 6B.

Figure 1A:
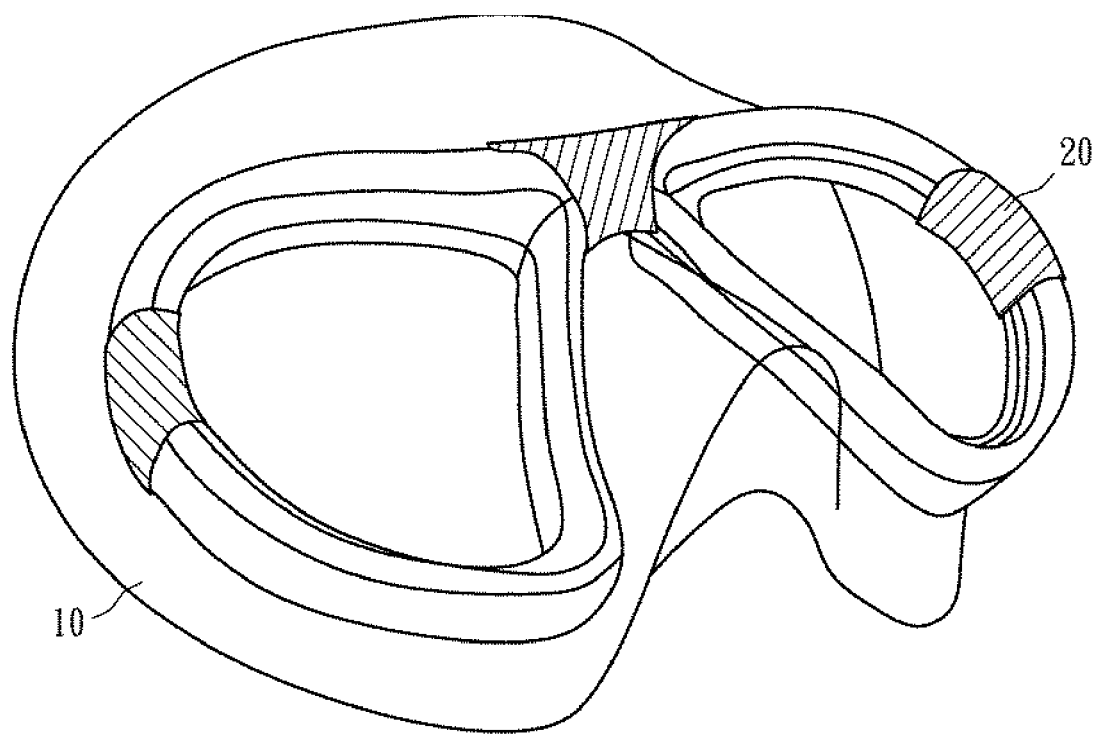
FIG. 1A and FIG. 1B are schematic views of a conventional diving goggle.
Figure 1B:
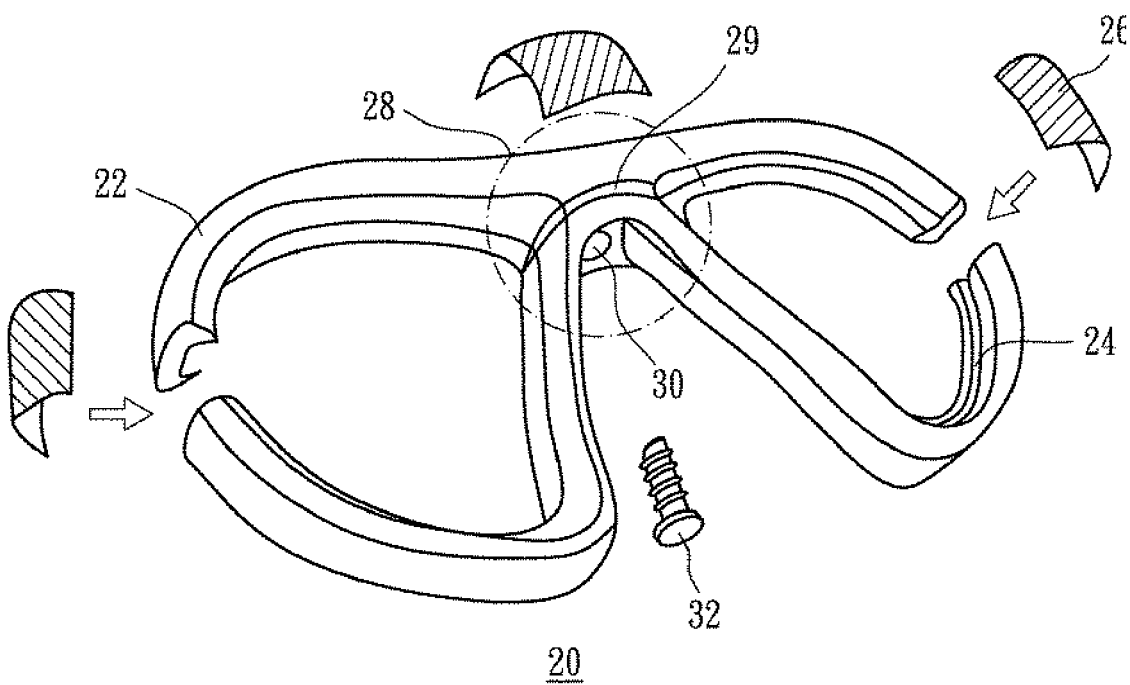

It should be noted that although some gaps may be disposed in the main body of the frame structure in the above implementations, the main body will not suffer from water leakage. The reason mainly lies in that the frame structure of this invention is integrally molded, adhered or assembled in other appropriate manners so that there are no crevices in the nose portion of the main body. Furthermore, because the conventional fixing mount 30 and the locking device 32, as shown in FIG. 1B, are eliminated in the nose portion of the main body of this invention, the number of parts in the goggle are reduced, which helps to avoid to loss of parts and reduce the costs.

Additionally, the aforesaid frame structure with two lens is only one of the several embodiments of this invention, but not intended to limit the scope of this invention. Alterations may be readily made thereto by those skilled in the art upon reading the above description. In other words, the hard portion A and the soft portion B in the frame structure of this invention can together define at least one receiving space for at least one lens.

Figure 7A:
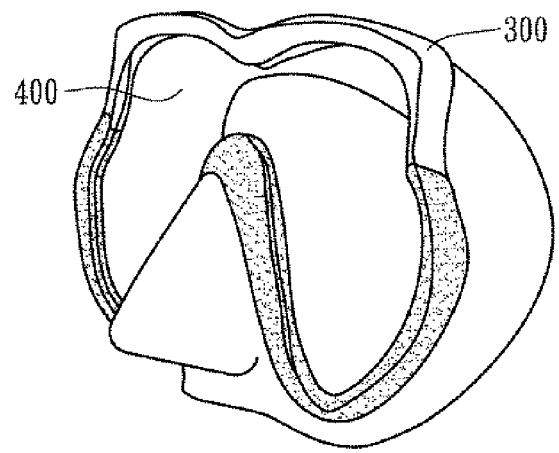
FIGS. 7A to 7C are schematic views of a single-lens, a triple-lens and a quadruple-lens frame structure of this invention respectively.
Figure 7B:
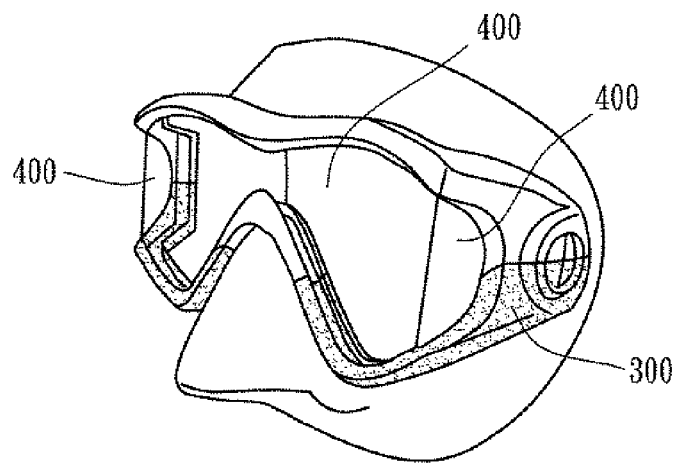
Figure 7C:
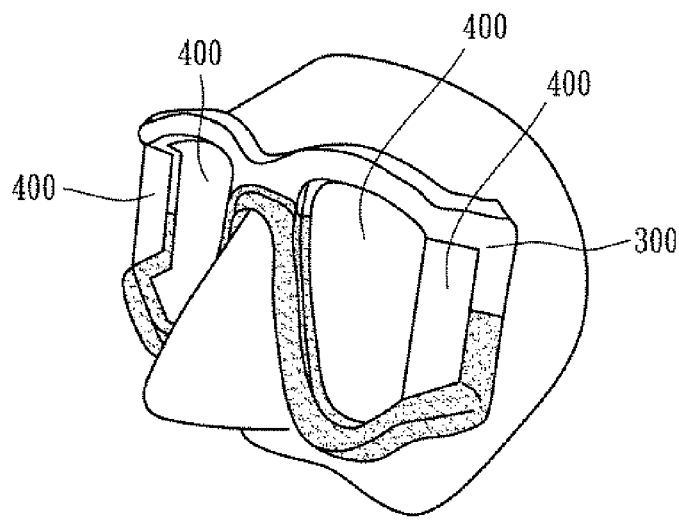

Depending on the number of lens pieces actually used, the frame structure of this invention may be designed as a single-lens frame structure, a dual-lens frame structure, a triple-lens frame structure or a quadruple-lens frame structure. As shown in FIG. 7A, the frame structure depicted therein is a single-lens frame structure 300, in which the hard portion A and the soft portion B together define a receiving space 320 for receiving a single lens 400. As shown in FIG. 7B, the frame structure depicted therein is a triple-lens frame structure 300, in which the hard portion A and the soft portion B together define a receiving space 320 for receiving three lenses 400 including two side lenses. As shown in FIG. 7C, the frame structure depicted therein is a quadruple-lens frame structure 300, in which the hard portion A and the soft portion B together define two receiving spaces 320 for receiving the lenses 400 including the two side lenses. The single-lens, triple-lens and quadruple-lens frame structures depicted respectively in FIG. 7A to FIG. 7C all have the same technical features as the aforesaid dual-lens frame structure, and therefore will not be described in detail herein.

The above embodiments are only intended to illustrate the principle and efficacy of the subject invention, and not to limit the subject invention. Any people skilled in this field may proceed with modifications and changes to the above examples without departing from the technical principle and spirit of the subject invention. Therefore, the scope of protection of the subject invention is covered in the following claims as appended.

What is claimed is:

1. A frame structure, including a main body, the main body comprising:
   a hard portion, which is a rigid body, the hard portion comprising an upper bridge portion and a nose portion extending downward from a central area of the upper bridge portion; and
   a soft portion, which is an elastomer being molded with the hard portion integrally, the soft portion comprising a frame portion including a first frame and a second frame, wherein the first frame is formed at a side of the upper bridge portion and the nose portion, and the second frame is formed at an opposite side of the upper bridge portion and the nose portion;
   wherein each of the first frame and the second frame connects with the upper bridge portion and the nose portion to define a receiving space for securing a lens therein in a sealing manner.

2. The frame structure of claim 1, wherein the hard portion is made of materials selected from a group consisting of polycarbonate (PC), polyethylene (PE), polyoxomethylene (POM), resin, acrylic, polyurethane (PU), polyvinyl chloride (PVC), acrylonitrile butadiene styrene (ABS), polypropylene (PP), nylon, metals and their combination.

3. The frame structure of claim 1, wherein the soft portion is made of materials selected from a group consisting of thermoplastic rubber (TPR), thermoplastic polyurethane (TPU), thermoplastic elastomer (TPE), polyurethane (PU), polyvinylchloride (PVC), silicone, nature rubber and their combination.

4. The frame structure of claim 1, wherein the soft and the hard portions are formed by overmolding.

5. The frame structure of claim 1, wherein the soft and the hard portions are formed by multi-material injection molding.

6. The frame structure of claim 1, wherein the main body further comprises a first gap and a second gap disposed thereon wherein the first gap is formed between the upper bridge portion and the first frame, and the second gap is formed between the upper bridge portion and the second frame.

7. The frame structure of claim 6, further comprising a first joint and a second joint, wherein the first joint and the second joint are respectively received within the first gap and the second gap.

8. The frame structure of claim 1, wherein the hard and the soft portions define one receiving space, adapted to receive one lens.

9. The frame structure of claim 1, wherein the hard and the soft portions define one receiving space, adapted to receive three lenses.

10. The frame structure of claim 1, wherein the hard and the soft portions define two receiving spaces, adapted to receive two lenses.

11. The frame structure of claim 1, wherein the hard and the soft portions define two receiving spaces, adapted to receive four lenses.

12. A frame structure for use in swimming goggles, including a main body, the main body comprising:
    a hard portion, which is a rigid body, the hard portion comprising an upper bridge portion and a nose portion extending downward from a central area of the upper bridge portion; and
    a soft portion, which is an elastomer, connecting to the hard portion, and the soft portion comprising a frame portion including a first frame and a second frame, wherein the first frame is formed at a side of the upper bridge portion and the nose portion, and the second frame is formed at an opposite side of the upper bridge portion and the nose portion;
    wherein each of the first frame and the second frame connects with the upper bridge portion and the nose portion to define a receiving space for securing a lens therein in a sealing manner.

13. The frame structure of claim 12, wherein the hard and the soft portions are molded integrally.

14. The frame structure of claim 12, wherein the soft portion is adhered to the hard portion with an adhesive.

* * * * *